(12) United States Patent
Deng et al.

(10) Patent No.: US 6,472,172 B1
(45) Date of Patent: Oct. 29, 2002

(54) DNA ENCODING A NOVEL HUMAN INHIBITOR-OF-APOPTOSIS PROTEIN

(75) Inventors: Gang Deng, Benicia; Jiing-Huey Lin, Alamo; Michael John Morser, San Francisco, all of CA (US)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/127,928

(22) Filed: Jul. 31, 1998

(51) Int. Cl.$^7$ .......................... C12P 21/00; C12N 15/00; C12N 15/09; C12N 15/63; C12N 15/70

(52) U.S. Cl. .................. 435/69.1; 435/320.1; 435/325; 530/300; 530/350; 536/1; 536/18.7; 536/22.1; 536/23.1; 536/23.4; 536/23.5

(58) Field of Search .................... 536/23.5, 1, 18.7, 536/22.1, 23.1, 23.4; 435/69.1, 325, 320.1; 530/300, 350

(56) References Cited

U.S. PATENT DOCUMENTS

| | | | |
|---|---|---|---|
| 5,919,912 A | * | 7/1999 | Korneluk et al. |
| 6,133,437 A | | 10/2000 | Korneluk et al. |
| 6,156,535 A | | 12/2000 | Korneluk et al. |
| 6,159,948 A | | 12/2000 | Robertson et al. |

FOREIGN PATENT DOCUMENTS

| | | | |
|---|---|---|---|
| WO | WO 96/35703 | * | 11/1996 |
| WO | WO 97/06182 | * | 2/1997 |
| WO | WO 97/06255 | * | 2/1997 |
| WO | WO 98/22131 | | 5/1998 |

OTHER PUBLICATIONS

Liston, P. et al., Suppression of apoptosis inmammalian cells by NAIP and a related family of IAP genes. Nature, 379: 349–353, Jan. 1996.*

Rothe, M. et al., The TNFR2–TRAF signalling complex contains two novel proteins related to baculoviral inhibitor of apoptosis proteins. Cell, 83: 1243–1252. Dec. 1995.*

Uren, A.G. et al., Cloning and expression of apoptosis inhibitory protein homologs that function to inhibit apoptosis and/or bind tumor necrosis factor receptor–associated factors. Proc. Natl. Acad. Sci. USA, 93: 4974–4978. May 1996.*

Ausubel, F.M. et al. Current Protocols in Molecular Biology. John Wiley & Sons, New York, pp. 2.2.1–2.2.3. 1990.*

Liston et al. "Life and death decisions: the role of the IAPs in modulating programmed cell death" Apoptosis (1997) 2:423–441.

Crook et al. "An apoptosis–inhibiting baculovirus gene with a zinc finger–like motif" J. of Virol. (1993) 67: 2168–2174.

Hay et al. "Drosophila homologs of baculovirus inhibitor of apoptosis proteins function to block cell death" (1995) Cell 83:1253–1262.

Ambrosini et al. "A novel anti–apoptosis gene, survivin, expressed in cancer and lymphoma" Nat. Med. (1997) 3:917–921.

Duckett et al. "A conserved family of cellular genes related to the baculovirus iap gene and encoding apoptosis inhibitors" (1996) Embo J. 15:2685–2694.

Thornberry, N.A. "The capase family of cysteine proteases" Br. Med. Bull. (1997) 53:478–490.

Resnicoff et al. "The baculovirus anit–apoptopic p35 protein promotes transformation of mouse embryo fibroblasts" J. Biol Chem. (1998) 273:10376–10380.

Rajcan–Separovic et al. "Assignment of Human Inhibitor of Apoptosis Protein (IAP) Genes xiap, hiap 1, and hiap–2 to Chromosomes Xq25 and 11q22–q23 by Fluorescence in Situ Hybridization" Genomics (1996) 37:404–406.

Young et al. "Genomic organization and physical map of the human inhibitors of apoptosis: HIAP1 and HIAP2" Mammalian Genome (1999) 10: 44–48.

Lin et al., "KIAP, a Novel Member of the Inhibitor of Apoptosis Protein Family", Biochem Biophys. Res. Comm. (2000) 279:820–831.

Vucic et al., "ML–IAP, a novel inhibitor of apoptosis that is preferentially expressed in human melanomas", Current Biology (2000) 10:1359–1366.

Ambrosini et al., "Induction of Apoptosis and Inhibition of Cell Proliferation by survivin Gene Targeting", J. Biol. Chem. (1998) 273(18):11177–11182.

Lu et al., "Expression of a Novel Antiapoptosis, Survivin, Correlated with Tumor Cell Apoptosis and p53 Accumulation in Gastric Carcinomas", Cancer Research 58:1808–1812.

Adida et al., "Anti–apoptosis gene, survivin, and prognosis of neuroblastoma", The Lancet (1998) 351:882–883.

Roy et al., "The c–IAP–1 and c–IAP–2 proteins are direct inhibitors of specific caspases" EMBO J. (1997) 16(23):6914–6925.

* cited by examiner

Primary Examiner—Anthony C. Caputa
Assistant Examiner—Alana M. Harris
(74) Attorney, Agent, or Firm—Wendy L. Washtien

(57) ABSTRACT

The present invention relates to novel human inhibitor-of-apoptosis polypeptides, designated HIAP3, polynucleotides encoding the polypeptides, methods for producing the polypeptides, expression vectors and genetically engineered host cells for expression of the polypeptides. The invention further relates to methods for utilizing the polynucleotides and polypeptides in research, diagnosis, and therapeutic applications.

17 Claims, 5 Drawing Sheets

Fig. 1 Polynucleotide sequence of *hiap3*

```
          10         20         30         40         50         60
GGGATACTCC CCTCCCAGGG TGTCTGGTGG CAGGCCTGTG CCTATCCCTG CTGTCCCCAG
          70         80         90        100        110        120
GGTGGGCCCC GGGGGTCAGG AGCTCCAGAA GGGCCAGCTG GCATATTCT  GAGATTGGCC
         130        140        150        160        170        180
ATCAGCCCCC ATTTCTGCTG CAAACCTGGT CAGAGCCAGT GTTCCCTCCA TGGGACCTAA
         190        200        210        220        230        240
AGACAGTGCC AAGTGCCTGC ACCGTGGACC ACAGCCGAGC CACTGGGCAG CCGGTGATGG
         250        260        270        280        290        300
TCCCACGCAG GAGCGCTGTG GACCCCGCTC TCTGGGCAGC CCTGTCCTAG GCCTGGACAC
         310        320        330        340        350        360
CTGCAGAGCC TGGGACCACG TGGATGGGCA GATCCTGGGC CAGCTGCGGC CCCTGACAGA
         370        380        390        400        410        420
GGAGGAAGAG GAGGAGGGCG CCGGGGCCAC CTTGTCCAGG GGGCCTGCCT TCCCCGGCAT
         430        440        450        460        470        480
GGGCTCTGAG GAGTTGCGTC TGGCCTCCTT CTATGACTGG CCGCTGACTG CTGAGGTGCC
         490        500        510        520        530        540
ACCCGAGCTG CTGGCTGCTG CCGGCTTCTT CCACACAGGC CATCAGGACA AGGTGAGGTG
         550        560        570        580        590        600
CTTCTTCTGC TATGGGGGCC TGCAGAGCTG GAAGCGCGGG GACGACCCCT GGACGGAGCA
         610        620        630        640        650        660
TGCCAAGTGG TTCCCCAGCT GTCAGTTCCT GCTCCGGTCA AAAGGAAGAG ACTTTGTCCA
         670        680        690        700        710        720
CAGTGTGCAG GAGACTCACT CCCAGCTGCT GGGCTCTTGG GACCCGTGGG AAGAACCGGA
         730        740        750        760        770        780
AGACGCAGCC CCTGTGGCCC CCTCCGTCCC TGCCTCTGGG TACCCTGAGC TGCCCACACC
         790        800        810        820        830        840
CAGGAGAGAG GTCCAGTCTG AAAGTGCCCA GGAGCCAGGA GGGGTCAGTC CAGCCGAGGC
         850        860        870        880        890        900
CCAGAGGGCG TGGTGGGTTC TTGAGCCCCC AGGAGCCAGG GATGTGGAGG CGCAGCTGCG
         910        920        930        940        950        960
GCGGCTGCAG GAGGAGAGGA CGTGCAAGGT GTGCCTGGAC CGCGCCGTGT CCATCGTCTT
         970        980        990       1000       1010       1020
TGTGCCGTGC GGCCACCTGG TCTGTGCTGA GTGTGCCCCC GGCCTGCAGC TGTGCCCCAT
        1030       1040       1050       1060       1070       1080
CTGCAGAGCC CCCGTCCGCA GCCGCGTGCG CACCTTCCTG TCCTAGGCCA GGTGCCATGG
        1090       1100       1110       1120       1130       1140
CCGGCCAGGT GGGCTGCAGA GTGGGCTCCC TGCCCCTCTC TGCCTGTTCT GGACTGTGTT
        1150       1160       1170       1180       1190       1200
CTGGGCCTGC TGAGGATGGC AGAGCTGGTG TCCATCCAGC ACTGACCAGC CCTGATTCCC
        1210       1220       1230       1240       1250       1260
CGACCACCGC CCAGGGTGGA GAAGGAGGCC CTTGCTTGGC GTGGGGATG  GCTTAACTGT
        1270       1280       1290       1300       1310       1320
ACCTGTTTGG ATGCTTCTGA ATAGAAATAA AGTGGGTTTT CCCTGGAGGT ACCCAGCAAA
        1330       1340       1350       1360       1370       1380
AAAAAAAAAA AAAAAA...  ..........  ..........  ..........  ..........
```

Fig. 2 Deduced amino acid sequence of HIAP3

```
  1  MGPKDSAKCLHRGPQPSHWAAGDGPTQERCGPRSLGSPVLGLDTCRAWDHVDGQILGQLR   60
 61  PLTEEEEGAGATLSRGPAFPGMGSEELRLASFYDWPLTAEVPPELLAAAGFFHTGHQD    120
121  KVRCFFCYGGLQSWKRGDDPWTEHAKWFPSCQFLLRSKGRDFVHSVQETHSQLLGSWDPW  180
181  EEPEDAAPVAPSVPASGYPELPTPRREVQSESAQEPGGVSPAEAQRAWWVLEPPGARDVE  240
241  AQLRRLQEERTCKVCLDRAVSIVFVPCGHLVCAECAPGLQLCPICRAPVRSRVRTFLS    298
```

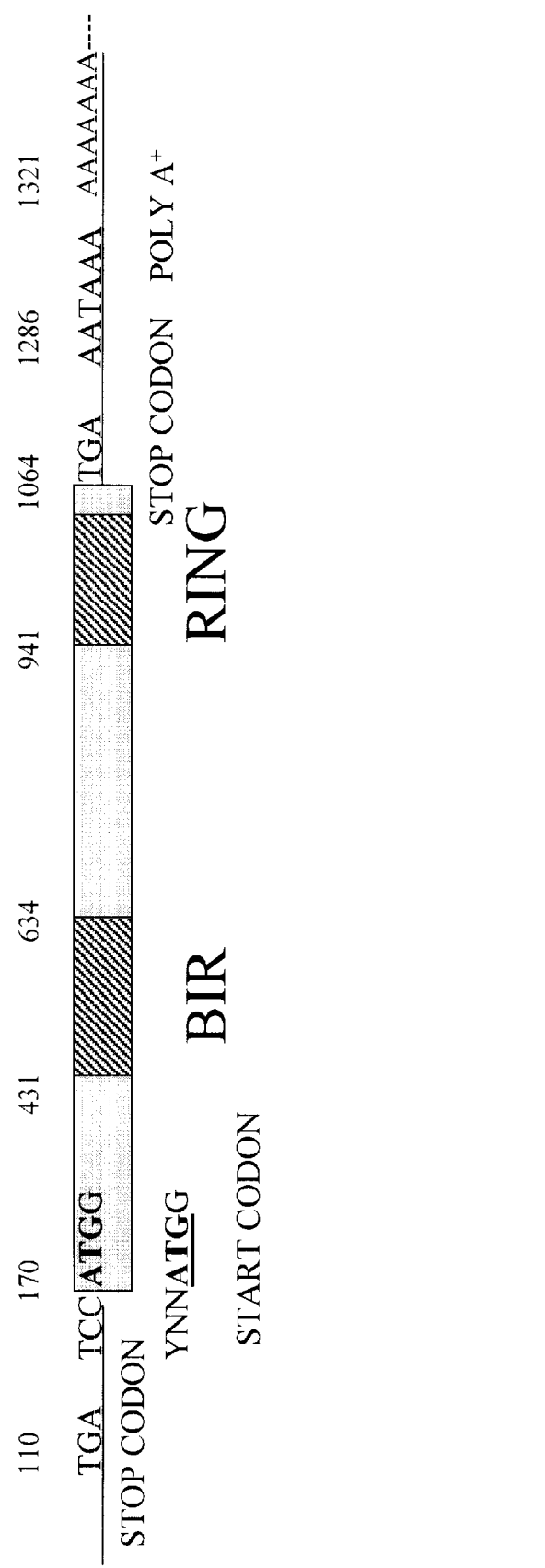
Fig. 3 *hiap3* cDNA

Fig.4 Alignment of BIR Domain in IAP proteins

```
iapx_human    EARIFTFGTW IYS--VNKEQ LARAGFYALG EGDKVKCFHC GGGLTDWKPS EDPW.E.QHA KWYPGCKYLL
HIAP3_human   ELRLASFYDW PLTAEVPPEL LAAAGFFHTG HQDKVRCFFC YGGLQSWKRG DDPWTE..HA KWFPSCQFLL
iap2_mouse    SARLRTFLYW PPSVPVQPEQ LASAGFYYVD RNDDVKCFCC DGGLRCWEPG DDPWIE..HA KWFPRCEFLI
iap2_human    AARMRTEMYW PSSVPVQPEQ LASAGFYYVG RNDDVKCFCC DGGLRCWESG DDPWIE..HA KWFPRCEFLI
iap_chick     EARVKTFINW PTRIPVQPEQ LADAGFYYVG RNDDVKCFCC DGGLRCWESG DDPWIE..HA KWFPRCEYLL
iap1_human    AARFKTFFNW PSSVLVNPEQ LASAGFYYVG NSDDVKCFCC DGGLRCWESG DDPWVQ..HA KWFPRCEYLI
iap1_mouse    AARIRTFSNW PSSALVHSQE LASAGFYYTG HSDDVKCFCC DGGLRCWESG DDPWVE.SHA KWFPRCEYLL
iap3_npvop    AARLRTFAEW PRGLKQRPEE LAEAGFFYTG QGDKTRCFCC DGGLKDWEPD DAPWQQ..HA RWYDRCEYVL
iap_fvcp      AARVKSFHNW PRCMKQRPEQ MADAGFFYTG YGDNTKCFYC DGGLKDWEPE DVPWEQ..HV RWFDRCAYVQ
iap2_drome    DARLRTFTDW PISNIQPASA LAQAGLYYQK IGDQVRCFHC NIGLRSWQKE DEPWFE..HA KWSPKCQFVL Consensus     -ARL-TF--W P-------- LA-AGFYYTG --D-V-CF-C -GGL--W--- D-PW----H- KW-P-C----
Cys/His       ---------- ---------- ---------- ------C--C ---------- --------H- -------C---
```

Fig. 5 Alignment of RING Domain in IAP Proteins

```
iapx_mouse    KLCKICMDRN  IAIVFVPCGH  LVTCKQCAEAV  DK.CPMCTTV
iapx_human    KLCKICMDRN  IAIVFVPCGH  LVTCKQCAEAV  DK.CPMCTTV
iap1_mouse    RMCKVCMDRE  VSIVFIPCGH  LVVCQECAPSL  RK.CPICRGI
iap2_mouse    RTCKVCMDRE  VSIVFIPCGH  LVVCQECAPSL  RK.CPICRGT
iap2_human    RTCKVCMDKE  VSVVFIPCGH  LVVCQECAPSL  RK.CPICRGT
iap1_human    RTCKVCMDKE  VSIVFIPCGH  LVVCQECAPSL  RK.CPICRGI
HIAP3_human   RTCKVCLDRA  VSIVFVPCGH  LV.CAECAPGL  QL.CPICRAP
iap_npvop     RLCKICLGAE  KTVCFVPCGH  VVACGKCAAGV  TT.CPVCRGQ
iap2_drome    RLCKVCLDEE  VGVVFLPCGH  LATCNQCAPSV  AN.CPMCRAD
traf2_human   LRCQQCQAEA  KCPKLLPCLH  TL.CSGCLEAS  GMQCPICQAP
consensus     --C--C----  --------C-H  -------C--C  ----C---
```

DNA ENCODING A NOVEL HUMAN INHIBITOR-OF-APOPTOSIS PROTEIN

FIELD OF THE INVENTION

This invention relates, in part, to newly identified polynucleotides and polypeptides; variants and derivatives of the polynucleotides and polypeptides; methods of making the polynucleotides and polypeptides, and their variants and derivatives; and uses of the polynucleotides, polypeptides, variants, and derivatives. In particular, in these and in other regards, the invention relates to novel human inhibitor-of-apoptosis polypeptides and the polynucleotides which encode these polypeptides.

BACKGROUND OF THE INVENTION

Apoptosis, also known as programmed cell death, is a genetically controlled process which plays an important role in development and in cellular and tissue homeostasis (Hengartner, M., *Exp. Gerontol.* 32: 363–374, 1997; Hoeppner et al., *Biochem. Biophys. Acta* 1242:217–220, 1996; Ellis et al., *Annual Rev. Cell Biol.* 7:663–698, 1991). Apoptosis permits the elimination of cells which either have been overproduced, developed improperly or have undergone genetic damage and represents a major host defense mechanism for limiting the replication of infective viruses. In contrast to necrotic cell death, which is usually accompanied by swelling and disruption of cellular membranes and inflammation of adjacent tissue, apoptosis is marked by cell shrinkage, blebbing, chromatin condensation, DNA fragmentation and formation of apoptotic bodies (MacLellan and Schneider, *Circ. Res.* 81:137–144, 1997; Cohen, G., *Biochem. J.* 326 (Pt 1):1–16, 1997). Apoptotic cells are then phagocytosed by neighboring scavenger cells without eliciting an inflammatory response (Wu and Horvitz, *Nature* 392:501–504, 1998).

Deregulation of apoptosis has been implicated in the pathogenesis of a variety of diseases. Impaired apoptosis can play a role in cancer (Pan et al., *Cancer Surv.* 29:305–327, 1997; Thompson, C., *Science* 267:1456–1462, 1995) or chronic viral infection (Clem et al., *Science* 254:1388–1390, 1991; Clem and Miller, *Mol. Cell. Biol.* 14:5212–5222, 1994). Inappropriate (or premature) apoptosis may contribute to neurodegenerative disorders (Roy et al., *Cell* 80:167–178, 1995; Raff et al., *Science* 262:695–700, 1996) or acquired immunodeficiency disease (Banda, N., *J. Exp. Med.* 176:1099–1106, 1992). Premature apoptosis is also recognized as a contributing cause of myocyte loss in ischemia/repurfusion injury, myocardial infarction (MacLellan and Schneider, *Circ. Res.* 81:137–144, 1997), and congestive heart failure (Feuerstein, G., *Trends Cardiovas. Med.* 7:249–255, 1997).

The presence of a novel class of apoptosis inhibitors, known as inhibitor of apoptosis proteins (IAPs) has been reported in the literature (Liston et al., *Apoptosis* 2:423–441, 1997). The first IAP was discovered in baculovirus (Crook et al., *J. Vir. 67:2166–2174, 1993*) and IAPs have now been reported in Drosophila, chick, mouse and human (Hay et al., *Cell* 83:1253–1262, 1995; Liston et al., supra). Five human IAPs have been identified: HIAP1, HIAP2, XIAP (X-chromosome linked IAP), NIAP (neuronal IAP) and survivin (Ambrosini et al., *Nat. Med.* 3:917–921, 1997; Duckett et al., *Embo J.* 15:2685–2694, 1996).

IAPs are a highly evolutionarily conserved family of proteins, containing a number of common structural features (domains). Among these are an N-terminal domain containing one or more repeats of a domain referred to as the BIR (baculovirus IAP repeat) domain (Liston et al., supra), and a C-terminal RING zinc finger domain. These domains are present to varying degrees within the known members of the IAP family; HIAP1 and HIAP2 contain three BIR domains and a C-terminal RING domain, while survivin contains only a single BIR domain and no RING domain.

While the physiological role of IAPs is not exactly clear, some members of the IAP family appear to play a regulatory role in apoptosis. Recombinant IAPs were found to suppress apoptosis induced by a variety of stimuli in different cell types. Drosophila IAPs (DIAP1 and DIAP2) were found to interact with a Decapentaplegic (Dpp) type I receptor, suggesting that these DIAPs may act as negative regulators of the Dpp signaling pathway, which normally leads to cell apoptosis. XIAP, HIAP1 and HIAP2 can directly inhibit specific caspases (cysteine containing aspartate specific proteases), enzymes which are involved in the pathways which control apoptosis, and thereby suppress apoptosis (Thornberry, N., *Br. Med. Bull.* 53:478–490, 1997). However, NIAP was found not to inhibit caspases, suggesting that different IAPs may have different mechanisms of action.

By helping in the regulation of programmed cell death, IAPs play an important role in the maintenance of the appropriate life cycle of the various cells of an organism. It is likely that variance from normal levels (either overabundance or deficiency) of IAPs within the cellular environment may lead to conditions in vivo which are related to various disease states.

IAPs may play a role in tumor formation. Up-regulated chicken IAP and concomitant suppression of apoptosis were found in chicken cells transformed by the oncoprotein v-rel, a member of the Rel/NF$_{kappa}$B family (You et al., *Mol. Cell. Biol.* 17:7328–7341, 1997). Similarly, baculovirus protein p35 (a baculovirus IAP) is capable of promoting the transformation of mouse embryo fibroblasts in the presence of the insulin-like growth factor I receptor (Resnicoff et al., *J. Biol. Chem.* 273:10376–10380, 1998).

Survivin is undetectable in terminally differentiated adult tissues but expressed in all common human cancers, further suggesting that apoptosis inhibition may be a general feature of neoplasia (Ambrosini et al., supra).

Deletion mutations in human NIAP have been linked to inappropriate depletion of motor neurons associated with spinal muscular atrophy, an autosomal neurodegenerative disorder (Xu et al., *J. Comp. Neurol.* 382:247–259, 1997). In a rat ischemia model, in vivo overexpression of NIAP reduced ischemic damage in the rat hippocampus (Roy et al., supra), indicating that the presence of increased levels of IAPs could prevent the unwanted cell death characteristic of ischemia and that elevating the neuronal levels of this IAP may be useful in treating stroke.

Finally, Stellar and his colleagues were able to block retinal cell death and show significant retention of visual function in Drosophila which exhibited retinitus pigmentosa, a cause of blindness in humans, by eye-specific expression of the antiapoptotic protein p35 (Davidson and Stellar, *Nature* 391:587–591, 1998).

These data suggest that antiapoptotic proteins, such as IAPs, are good candidates for use in the therapeutic intervention of diseases caused by altered apoptosis.

There is a need, therefore, for identification and characterization of proteins that influence apoptosis. In particular, there is a need to isolate and characterize additional IAPs, akin to known IAPs, which may be employed, therefore, for ameliorating or correcting dysfunctions or disease associated with inappropriate apoptosis; in cancer and chronic viral infections, where IAPs may be overproduced, as well as in neurodegenerative disorders, chronic heart failure and dysfunctional immune response, where a deficiency in IAPs may exist.

SUMMARY OF THE INVENTION

The present invention provides a polynucleotide sequence which uniquely encodes a novel human inhibitor-of-apoptosis protein. Designated HIAP3, the polypeptide is characterized by structural features common to the inhibitor-of-apoptosis protein family, such as BIR and RING domains. The polynucleotide sequence, designated in lower case, hiap3, and described in FIG. 1 (SEQ ID NO:1) encodes the amino acid sequence, which is designated HIAP3, and is shown in FIG. 2 (SEQ ID NO:2).

Toward these ends, and others, it is an object of the present invention to provide polypeptides, inter alia, that have been identified as a novel HIAP3 by homology between the amino acid sequence set out in FIG. 2 (SEQ ID NO: 2) and known amino acid sequences of other IAP proteins.

It is a further object of the invention, moreover, to provide polynucleotides that encode HIAP3, particularly polynucleotides that encode the polypeptide herein designated HIAP3.

In accordance with this aspect of the invention there are provided isolated polynucleotides encoding HIAP3, including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of hiap3 polynucleotides.

It also is an object of the invention to provide HIAP3 polypeptides that may be employed to treat neoplasia, neurodegenerative disorders, immune disorders, chronic viral infections, or chronic heart failure.

In accordance with this aspect of the invention there are provided novel polypeptides of human origin referred to herein as HIAP3 as well as biologically, diagnostically or therapeutically useful fragments, variants and derivatives thereof, variants and derivatives of the fragments, and analogs of the foregoing.

Among the particularly preferred embodiments of this aspect of the invention are variants of HIAP3 encoded by naturally occurring allelic variants of the hiap3 polynucleotide.

It is another object of the invention to provide a method of producing the aforementioned polypeptides, polypeptide fragments variants and derivatives, fragments of the variants and derivatives, and analogs of the foregoing. In a preferred embodiment of this aspect of the invention there are provided methods of producing the aforementioned HIAP3 polypeptides comprising culturing host cells having expressibly incorporated therein an exogenously-derived HIAP3-encoding polynucleotide under conditions for expression of human HIAP3 in the host and then recovering the expressed polypeptide.

In accordance with another object of the invention there are provided products, compositions, processes and methods that utilize the aforementioned polypeptides and polynucleotides for research, biological, clinical and therapeutic purposes, inter alia.

In accordance with certain preferred embodiments of this aspect of the invention, there are provided products, compositions and methods, inter alia, for, among other things: assessing HIAP3 expression in cells by determining HIAP3 polypeptides or HIAP3-encoding mRNA; assaying genetic variation and aberrations, such as defects, in hiap3 genes; and administering an HIAP3 polypeptide or polynucleotide encoding HIAP3 to an organism to alter the level of HIAP3 activity.

In accordance with certain preferred embodiments of this and other aspects of the invention there are provided probes that hybridize to hiap3 sequences.

In certain additional preferred embodiments of this aspect of the invention there are provided antibodies against HIAP3 polypeptides. In certain particularly preferred embodiments in this regard, the antibodies are highly selective for HIAP3, and may be employed diagnostically to detect increased HIAP3 expression, which may be associated with conditions in which inhibition of apoptosis is too strong, such as cancer.

In a further aspect of the invention there are provided compositions comprising an hiap3 polynucleotide or an HIAP3 polypeptide for administration to cells in vitro, to cells ex vivo and to cells in vivo, or to a multicellular organism. In certain particularly preferred embodiments of this aspect of the invention, the compositions comprise an hiap3 polynucleotide for expression of an HIAP3 polypeptide in a host organism for treatment of disease. Particularly preferred in this regard is expression in a human patient for treatment of a disease state which is alleviated by increasing the level of HIAP3 activity.

In a further aspect of the invention there are provided ribozymes and polynucleotides complementary to hiap3 polynucleotides (i.e. antisense polynucleotides) for administration to cells in vitro, to cells ex vivo and to cells in vivo, or to a multicellular organism. Particularly preferred in this regard is administration to a human patient for treatment of a disease state which is alleviated by decreasing the level of HIAP3 activity.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following. description and from reading the other parts of the present disclosure.

BRIEF DESCRIPTION OF THE DRAWINGS

FIG. 1 displays the polynucleotide sequence of hiap3 (SEQ ID NO: 1), which encodes HIAP3.

FIG. 2 displays the deduced amino acid sequence of HIAP3 (SEQ ID NO: 2).

FIG. 3 displays a schematic drawing of the functional domains within an HIAP3 polypeptide.

FIG. 4 demonstrates the amino acid alignment of the BIR domain of HIAP3 with the BIR domain of other members of the IAP protein family.

FIG. 5 demonstrates the amino acid alignment of the RING domain of HIAP3 with the RING domain of other members of the IAP protein family.

The following drawings depict certain embodiments of the invention. They are illustrative only and do not limit the invention otherwise disclosed herein.

DETAILED DESCRIPTION OF THE INVENTION

Definitions

As used in the specification, examples and appended claims, unless specified to the contrary, the following terms have the meaning indicated.

"HIAP3" refers to the polypeptide having the amino acid sequence set out in FIG. 2 (SEQ ID NO:2) variants, analogs, derivatives and fragments thereof, and fragments of the variants, analogs and derivatives. The terms "fragment," "derivative" and "analog" when referring to the polypeptide of FIG. 2 (SEQ ID NO: 2) mean a polypeptide which retains essentially the same biological activities as the polypeptide of FIG. 2 (SEQ ID NO: 2).

"hiap3" refers to the polynucleotide having the sequence set out in FIG. 2 (SEQ ID NO: 1) and polynucleotides encoding polypeptides having the amino acid sequence of HIAP3 set out in FIG. 2 (SEQ ID NO: 2); and to polynucleotides encoding HIAP3 variants, analogs, derivatives and fragments, and fragments of the variants, analogs and derivatives. hiap3 also refers to such polynucleotides composed of RNA as well as to polynucleotides which are the complement of polynucleotides which encode the polypeptide sequence set out in FIG. 2 (SEQ ID NO: 2).

"Polynucleotide(s)" generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritium-labelled bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

"Polypeptides", as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present invention are, to name an illustrative few, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance, I. E. Creighton, *Proteins-Structure and Molecular Properties,* 2nd Ed., W. H. Freeman and Company, New York, 1993. Many detailed reviews are available on this subject, such as, for example, those provided by Wold, F., in *Posttranslational Covalent Modification of Proteins,* B. C. Johnson, Ed., Academic Press, New York, pp 1–12, 1983; Seifter et al., *Meth. Enzymol.* 182: 626–646, 1990 and Rattan et al., *Protein Synthesis: Posttranslational Modifications and Aging,* Ann. N.Y. Acad. Sci. 663: 48–62, 1992.

It will be appreciated, as is well known and as noted above, that polypeptides are not always entirely linear. For instance, polypeptides may be branched as a result of ubiquitination, and they may be circular, with or without branching, generally as a result of posttranslational events, including natural processing events and events brought about by human manipulation which do not occur naturally. Circular, branched and branched circular polypeptides may be synthesized by non-translational natural processes and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli,* prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation, inter alia. Similar considerations apply to other modifications.

It will be appreciated that the same type of modification may be present to the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

"Polynucleotide encoding a polypeptide" as used herein encompasses polynucleotides which include a sequence encoding a polypeptide of the present invention, particularly the HIAP3 having the amino acid sequence set out in FIG. 2 (SEQ ID NO: 2). The term encompasses polynucleotides that include a single continuous region or discontinuous regions encoding the polypeptide (for example, interrupted by introns) together with additional regions.

"Biological activity" refers to the biologic and/or immunologic activities of naturally occurring HIAP3.

"Oligonucleotide(s)" refers to relatively short polynucleotides. Often the term refers to single-stranded deoxyribonucleotides but it can refer as well to single- or double-stranded ribonucleotides, RNA:DNA hybrids and double-stranded DNAs, among others. Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms. "Oligonucleotides" or "oligomers" or polynucleotide "fragment", "portion", or "segment" refers to a polynucleotide sequence of at least about 10 nucleotides and as many as about 60 nucleotides, preferably about 15 to 30 nucleotides, and more preferably about 20–25 nucleotides.

"Naturally occurring HIAP3" refers to HIAP3 produced by human cells that have not been genetically engineered and specifically contemplates various HIAP3 forms arising from posttranslational modifications of the polypeptide including but not limited to acetylation, carboxylation, glycosylation, phosphorylation, lipidation and acylation.

"Variant(s)" of polynucleotides or polypeptides, as the term is used herein, are polynucleotides or polypeptides that differ from a reference polynucleotide or polypeptide, respectively. Variants in this sense are described below and elsewhere in the present disclosure in greater detail.

(1) A polynucleotide that differs in polynucleotide sequence from another, reference polynucleotide. Generally, differences are limited so that the polynucleotide sequences of the reference and the variant are closely similar overall and, in many regions, identical.

As noted below, changes in the polynucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the polynucleotide sequence of the variant may alter the amino acid sequence of a polypeptide encoded by the reference polynucleotide. Such polynucleotide changes may result in amino acid substitutions, additions, deletions, fusions and truncations in the polypeptide encoded by the reference sequence, as discussed below.

(2) A polypeptide that differs in amino acid sequence from another, reference polypeptide. Generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination. Recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations may also be introduced to modify the properties of the polypeptide, to change ligand-binding affinities, interchain affinities, or polypeptide degradation or turnover rate.

"Allelic variant" refers to an alternative form of the hiap3 polynucleotide. Alleles result from a mutation, i.e., a change in the polynucleotide sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of nucleotides. Each of these types of changes may occur alone, or in combination with the others, or one or more times in a given sequence.

"Derivative" refers to polynucleotides or polypeptides derived from naturally occurring hiap3 or HIAP3, respectively, by chemical modifications such as ubiquitination, labeling (e.g., with radionuclides, various enzymatic modifications), pegylation (derivatization with polyethylene glycol) or by insertion or substitution of amino acids such as ornithine (or substitution of the nucleotides which code for such as an amino acid), which do not normally occur in human proteins.

"Deletion" is defined as a change in either polynucleotide or amino acid sequences in which one or more polynucleotides or amino acid residues, respectively, are absent.

"Insertion" or "addition" is that change in a polynucleotide or amino acid sequence which has resulted in the addition of one or more polynucleotides or amino acid residues, respectively, as compared to the naturally occurring polynucleotide or amino acid sequence.

"Substitution" results from the replacement of one or more polynucleotides or amino acids by different polynucleotides or amino acids, respectively.

Preferably, amino acid substitutions are the result of replacing one amino acid with another amino acid having similar structural and/or chemical properties, such as the replacement of a leucine with an isoleucine or valine, an aspartate with a glutamate, or a threonine with a serine, i.e. conservative amino acid replacement. Insertions or deletions are typically in the range of about 1 to 5 amino acids. The variation allowed may be experimentally determined by systematically making insertions, deletions, or substitutions of amino acids in the polypeptide using recombinant DNA techniques and assaying the resulting recombinant variants for activity.

A polypeptide "fragment", "portion", or "segment" is a stretch of amino acid residues of at least about 5 amino acids, often at least about 7 amino acids, typically at least about 9 to 13 amino acids, and in various embodiments, at least about 17 or more amino acids.

"Recombinant" or "recombinant DNA molecule" refers to a polynucleotide sequence which is not naturally occurring, or is made by the artificial combination of two otherwise separated segments of sequence. By "recombinantly produced" is meant artificial combination often accomplished by either chemical synthesis means, or by the artificial manipulation of isolated segments of polynucleotides, e.g., by genetic engineering techniques. Such manipulation is usually done to replace a codon with a redundant codon encoding the same or a conservative amino acid, while typically introducing or removing a sequence recognition site. Alternatively, it is performed to join together polynucleotide segments with desired functions to generate a single genetic entity comprising a desired combination of functions not found in the common natural forms. Restriction enzyme recognition sites, regulation sequences, control sequences, or other useful features may be incorporated by design. "Recombinant DNA molecules" include cloning and expression vectors. "Recombinant" may also refer to a polynucleotide which encodes a polypeptide and is prepared using recombinant DNA techniques.

"Isolated" means altered "by the hand of man" from its natural state; i.e., that, if it occurs in nature, it has been changed or removed from its original environment, or both. For example, a naturally occurring polynucleotide or a polypeptide naturally present in a living animal in its natural state is not "isolated", but the same polynucleotide or polypeptide separated from the coexisting materials of its natural state is "isolated", as the term is employed herein. For example, with respect to polynucleotides, the term isolated means that it is separated from the chromosome and cell in which it naturally occurs. Polynucleotides and polypeptides may occur in a composition, such as media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

"Substantially pure" and "substantially homogenous" are used interchangeably and describe HIAP3 polypeptide, or fragments thereof, or a DNA segment encoding same, where such polypeptide or DNA molecule is separated from components that naturally accompany it. An HIAP3 polypeptide or fragment thereof, or DNA segment encoding same is substantially free of naturally-associated components when it is separated from the native contaminants which accompany it in its natural state. Thus, a polypeptide that is chemically synthesized or synthesized in a cellular system different from the cell in which it naturally originates will be substantially free from its naturally-associated components. Similarly, a polynucleotide that is chemically synthesized or synthesized in a cellular system different from the cell in which it naturally originated will be substantially free from its naturally-associated components.

"Homologous", when used to describe a polynucleotide, indicates that two polynucleotides, or designated sequences thereof, when optimally aligned and compared, are identical, with appropriate nucleotide insertions or deletions, in at least 70% of the nucleotides, usually from about 75% to 99%, and more preferably at least about 98 to 99% of the nucleotides.

"Polymerase chain reaction" or "PCR" refers to a procedure wherein specific pieces of DNA are amplified as described in U.S. Pat. No. 4,683,195, issued Jul. 28, 1987. Generally, sequence information from the ends of the polypeptide fragment of interest or beyond needs to be available, such that oligonucleotide primers can be designed; these primers will point towards one another, and will be identical or similar in sequence to opposite strands of the template to be amplified. The 5' terminal nucleotides of the two primers will coincide with the ends of the amplified material. PCR can be used to amplify specific DNA sequences from total genomic DNA, cDNA transcribed from total cellular RNA, plasmid sequences, etc. (See generally Mullis et al., *Cold Spring Harbor Symp. Quant. Biol.*, 51: 263, 1987; Erlich, ed., *PCR Technology*, Stockton Press, NY, 1989).

"Stringency" typically occurs in a range from about $T_m$ (melting temperature)–5° C. (50 below the $T_m$ of the probe) to about 20° C. to 25° C. below $T_m$. As will be understood by those of skill in the art, a stringency hybridization can be used to identify or detect identical polynucleotide sequences or to identify or detect similar or related polynucleotide sequences. As herein used, the term "stringent conditions" means hybridization will occur only if there is at least 95% and preferably at least 97% identity between the sequences.

"Hybridization" as used herein, shall include "any process by which a polynucleotide strand joins with a complementary strand through base pairing" (Coombs, J., *Dictionary of Biotechnology*, Stockton Press, New York, N.Y., 1994).

"Therapeutically effective dose" refers to that amount of polypeptide or its antibodies, antagonists, or inhibitors, including antisense molecules and ribozymes, which ameliorate the symptoms or conditions of a disease state. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$.

"Treating" or "treatment" as used herein covers the treatment of a disease-state in a human patient, which disease-state is associated with inappropriate apoptosis, and includes both disease states in which the patient is in need of decreased levels of HIAP3 and disease states in which the patient is in need of increased levels of HIAP3.

DETAILED DESCRIPTION OF THE INVENTION

The present invention relates to novel HIAP3 polypeptides and hiap3 polynucleotides, among other things, as described in greater detail below. In particular, the invention relates to novel HIAP3 polypeptides and the polynucleotides encoding these HIAP3 polypeptides, and relates especially to HIAP3 having the amino acid sequence set out in FIG. 2 (SEQ ID NO: 2) and hiap3 having the polynucleotide sequence set out in FIG. 1 (SEQ ID NO: 1). The present invention also encompasses HIAP3 variants. A preferred HIAP3 variant is one having at least 70% similarity (preferably at least 70% identity) to the polypeptide sequence shown in FIG. 2 (SEQ ID NO: 2) and more preferably at least 90% similarity (more preferably at least 90% identity) to the polypeptide shown in FIG. 2 (SEQ ID NO: 2) and still more preferably at least 95% similarity (still more preferably at least 95% identity) to the polypeptide sequence shown in FIG. 2 (SEQ ID NO: 2) and also includes portions of such polypeptides with such portion of the polypeptide generally containing at least 30 amino acids and more preferably at least 50 amino acids.

The polynucleotide sequence encoding a portion of HIAP3 was first identified as a 226 bp EST (expressed sequence tag; Incyte Clone #1419118) based on analysis of the Incyte EST database using the polypeptide consensus sequence of the BIR domain of IAPs and the BLAST database search program of the Genetic Computer Group package (Oxford Molecular Group, Campbell, Calif.). The chosen EST sequence demonstrated a 42% identity with the BIR domain of HIAP1 within a stretch of 57 amino acids. A full length cDNA was obtained by assembling the sequence of the original EST with sequences obtained using 3' and 5' RACE (rapid amplification of cDNA end) technology on a fetal kidney cDNA library and then using the assemble program of the GCG package. Database searching (both public and Incyte databases) identified an Incyte EST (Clone # 2953985), containing the 5' end of the polynucleotide sequence. This clone was obtained and sequenced.

The cDNA sequence designated hiap3 (SEQ ID NO: 1) contains 1337 base pairs. There are 169 bp in the 5' untranslated region and 274 bp in the 3' untranslated region flanking the coding region (see FIG. 1). The coding region consists of 894 nucelotides with an open reading frame of 298 amino acid residues. The initiation codon ATG is located at nucleotide position 170. Analysis of the deduced polypeptide sequence using the ScanProsite feature of the GCG package reveals a single BIR domain from amino acid position 88 to 155 and a RING zinc finger domain at positions 240 to 289.

The present invention is based in part on the structural homology shown in FIGS. 4 and 5 for the BIR and RING domains among HIAP3 and other members of the IAP protein family. There is approximately a 50% identity of the BIR domain between HIAP3 and the third BIR domain of either human or mouse IAP1 or IAP2. There is a 74% identity of the RING domain between HIAP3 and HIAP1. A Pile Up analysis shows very high homology within the members of the family as shown in FIGS. 4 and 5. Northern blot analysis indicated that the polynucleotide encoding HIAP3 is expressed mainly in placenta, lymph node, fetal kidney, and kidney tumor, giving it a tissue pattern distribution different from all other known human IAPs.

Polynucleotides

In accordance with one aspect of the present invention, there are provided isolated polynucleotides that encode the HIAP3 polypeptide having the deduced amino acid sequence of FIG. 2.

Using the information provided herein, such as the polynucleotide sequence set out in FIG. 1 (SEQ ID NO: 1) a polynucleotide of the present invention encoding an HIAP3 polypeptide may be obtained using standard cloning and screening procedures, such as those for cloning cDNAs using mRNA from cells of human tissue as starting material. Illustrative of the invention, the polynucleotide sequence in FIG. 1 (SEQ ID NO:1) was found in a human fetal kidney cDNA library.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIG. 1 (SEQ ID NO: 1). It also may be a polynucleotide with a different sequence, which, as a result of the redundancy (degeneracy) of the genetic code, encodes the polypeptide of FIG. 2.

Polynucleotides of the present invention which encode the polypeptide of FIG. 2 (SEQ ID NO: 2) may include, but are not limited to the coding sequence for the mature polypeptide, by itself; the coding sequence for the mature polypeptide and additional coding sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pcDNA3.1Myc-His vector (Invitrogen, Carlsbad, Calif.) among others, many of which are commercially available. As described in Gentz et al. (*Proc. Natl. Acad. Sci., USA* 86: 821–824, 1989), for instance, hexa-histidine provides for convenient purification of the fusion protein. The HA tag corresponds to an epitope derived from influenza hemagglutinin protein, which has been described by Wilson et al. (*Cell* 37: 767, 1984), for instance.

The present invention further relates to variants of the herein above described polynucleotides which encode for fragments, analogs and derivatives of the polypeptide having the deduced amino acid sequence of FIG. 2 (SEQ ID NO:2). A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by polynucleotide substitutions, deletions or additions. The substitutions, deletions or additions may involve one or more polynucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of HIAP3 set out in FIG. 2 (SEQ ID NO: 2), variants, analogs, derivatives and fragments thereof, and fragments of the variants, analogs and derivatives.

Further particularly preferred in this regard are polynucleotides encoding HIAP3 variants, analogs, derivatives and fragments, and variants, analogs and derivatives of the fragments, which have the amino acid sequence of the HIAP3 polypeptide of FIG. 2 (SEQ ID NO: 2) in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the HIAP3 polypeptide. Also especially preferred in this regard are conservative substitutions. Most highly preferred are polynucleotides encoding polypeptides having the amino acid sequence of FIG. 2 (SEQ ID NO: 2) without substitutions.

Further preferred embodiments of the invention are polynucleotides that are at least 70% identical to a polynucleotide encoding the HIAP3 polypeptide having the amino acid sequence set out in FIG. 2, and polynucleotides which are complementary to such polynucleotides. Alternatively, most highly preferred are polynucleotides that comprise a region that is at least 80% identical to a polynucleotide encoding the HIAP3 polypeptide and polynucleotides complementary thereto. In this regard, polynucleotides at least 90% identical to the same are particularly preferred, and among these particularly preferred polynucleotides, those with at least 95% are especially preferred. Furthermore, those with at least 97% are highly preferred among those with at least 95%, and among these, those with at least 98% and at least 99% are particularly highly preferred with at least 99% being the more preferred.

Particularly preferred embodiments in this respect, moreover, are polynucleotides which encode polypeptides which retain substantially the same biological activity as the mature polypeptide encoded by the polynucleotide sequence of FIG. 1 (SEQ ID NO: 1).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probes for cDNA and genomic DNA to isolate full-length cDNAs and genomic clones encoding HIAP3 and to isolate cDNA and genomic clones of other genes that have a high sequence similarity to the hiap3 gene. Such probes generally will comprise at least 15 bases. Preferably, such probes will have at least 30 bases and may have at least 50 bases. Particularly preferred probes will have at least 30 bases and will have 50 bases or less.

For example, the coding region of the hiap3 gene may be isolated by screening using the known DNA sequence to synthesize an oligonucleotide probe. A labeled oligonucleotide having a sequence complementary to that of a polypeptide of the present invention is then used to screen a library of human cDNA, genomic DNA or mRNA to determine to which members of the library the probe hybridizes.

The polynucleotides and polypeptides of the present invention may be employed as research reagents and materials for discovery of treatments and diagnostics to human disease as further discussed herein relating to polynucleotide assays, inter alia.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Polypeptides

The present invention further relates to an HIAP3 polypeptide which has the deduced amino acid sequence of FIG. 2 (SEQ ID NO: 2).

The invention also relates to fragments, analogs and derivatives of these polypeptides. The terms fragment, derivative and analog when referring to the polypeptide of FIG. 2 (SEQ ID NO: 2) means a polypeptide which retains essentially the same biological activity as such a polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

The fragment, derivative or analog of the polypeptide of FIG. 2 (SEQ ID NO:2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol) or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of HIAP3 set out in FIG. 2 (SEQ ID NO:2), variants, analogs, derivatives and fragments thereof, and variants, analogs and derivatives of the fragments. Alternatively, particularly preferred embodiments of the invention in this regard are polypeptides having the amino acid sequence of the HIAP3 shown in FIG. 2 (SEQ ID NO:2), variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics.

Typically seen as conservative substitutions are the replacements, one for another, among the aliphatic amino acids Ala, Val, Leu and Ile, interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

Further particularly preferred in this regard are variants, analogs, derivatives and fragments, and variants, analogs and derivatives of the fragments, having the amino acid sequence of the HIAP3 polypeptide of FIG. 2 in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the HIAP3. Also especially preferred in this regard are conservative substitutions. Most highly preferred are polypeptides having the amino acid sequence of FIG. 2 (SEQ ID NO:2) without substitutions.

The polypeptides and polynucleotides of the present invention are preferably provided in an isolated form, and preferably are purified to homogeneity.

The polypeptides of the present invention also include the polypeptide of FIG. 2 (SEQ ID NO:2) (in particular the mature polypeptide) as well as polypeptides which have at least 70% similarity (preferably at least 70% identity) to the polypeptide of FIG. 2 (SEQ ID NO:2) and more preferably at least 90% similarity (more preferably at least 90% identity) to the polypeptide of FIG. 2 (SEQ ID NO:2) and still more preferably at least 95% similarity (still more preferably at least 95% identity) to the polypeptide of FIG. 2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Fragments

Also among preferred embodiments of this aspect of the present invention are polypeptides comprising fragments of HIAP3, most particularly fragments of the HIAP3 having the amino acid sequence set out in FIG. 2 (SEQ ID NO:2), and fragments of variants and derivatives of the HIAP3 of FIG. 2 (SEQ ID NO:2).

In this regard a fragment is a polypeptide having an amino acid sequence that entirely is the same as part but not all of the amino acid sequence of the aforementioned HIAP3 polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of an HIAP3 polypeptide of the present invention comprised within a precursor polypeptide designed for expression in a host and having heterologous pre- and propolypeptide regions fused to the amino terminus of the HIAP3 fragment and an additional region fused to the carboxyl terminus of the fragment. Therefore, fragments in one aspect of the meaning intended herein, refers to the portion or portions of a fusion polypeptide or fusion protein derived from HIAP3.

As representative examples of polypeptide fragments of the invention, there may be mentioned those which have from about 25 to about 145 amino acids.

In this context about includes the particularly recited range and ranges larger or smaller by several, a few, 5, 4, 3, 2 or 1 amino acid at either extreme or at both extremes. For instance, about 145 amino acids in this context means a polypeptide fragment of 25 plus or minus several, a few, 5, 4, 3, 2 or 1 amino acids to 145 plus or minus several a few, 5, 4, 3, 2 or 1 amino acid residues, i.e., ranges as broad as 25 minus several amino acids to 145 plus several amino acids to as narrow as 25 plus several amino acids to 145 minus several amino acids.

Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 25 to about 145 amino acids.

Among especially preferred fragments of the invention are truncation mutants of HIAP3. Truncation mutants include HIAP3 polypeptides having the amino acid sequence of FIG. 2 (SEQ ID NO: 2), or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out above also are preferred embodiments of truncation fragments, which are especially preferred among fragments generally.

Also preferred in this aspect of the invention are fragments characterized by structural or functional attributes of HIAP3. Most preferred are fragments containing the BIR and C-terminal RING zinc finger domains of HIAP3.

Certain preferred regions in these regards are set out in FIG. 3, and include, but are not limited to, regions of the aforementioned types identified by analysis of the amino acid sequence set out in FIG. 2 (SEQ ID NO:2). As set out in FIG. 3, such preferred regions include the BIR domain and the C-terminal RING zinc finger domain.

Among highly preferred fragments in this regard are those that comprise regions of HIAP3 that combine several structural features, such as several of the features set out above. In this regard, the BIR and RING domains defined by the amino acid residues from about 88–155 and from about 240–289, respectively, of FIG. 2 (SEQ ID NO:2), which are characteristic of the IAP family of proteins are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of HIAP3. Most highly preferred in this regard are fragments that have a chemical, biological or other activity of HIAP3, including those with a similar activity or an improved activity, or with a decreased undesirable activity. Highly preferred in this regard are fragments that contain regions that are homologs in sequence, or in position, or in both sequence and position to active regions of related polypeptides, such as the other proteins of the IAP family, which includes HIAP3.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above.

Vectors, host cells, and expression systems

The present invention also relates to vectors which include polynucleotides of the present invention, host cells which are genetically engineered with vectors of the invention and the production of polypeptides of the invention by recombinant techniques. Such techniques are described in Sambrook et al., *Molecular Cloning, A Laboratory Manual*, Cold Spring Harbor Press, Plainview, N.Y., 1989 and Ausubel, F. M. et al., *Current Protocols in Molecular Biology*, John Wiley & Sons, New York, N.Y., 1989.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case, the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques. In accordance with this aspect of the invention, the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors, also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV4O, vaccinia viruses, adenoviruses, fowl pox viruses, pseudorabies viruses and retroviruses and vectors derived from combinations thereof, such as those derived from plasmid and bacteriophage genetic elements. such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those of skill, are set forth in great detail in Sambrook et al. cited elsewhere herein.

The DNA sequence in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs to name just a few of the well-known promoters. It will be understood that numerous promoters not mentioned are suitable for use in this aspect of the invention, are well known and may readily be employed by those of skill in the manner illustrated by the discussion and the examples herein.

In general, expression constructs will contain sites for transcription initiation and termination and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline, theomycin, kanamycin or ampicillin resistance genes for culturing *E. coli* and other bacteria.

The vector containing the appropriate DNA sequence as described elsewhere herein, as well as an appropriate promoter, and other appropriate control sequences, may be introduced into an host using a variety of well known techniques suitable to expression therein of a desired polypeptide. Representative examples of appropriate hosts include bacterial cells, such as *E. coli*. Streptomyces and *Salmonella typhimurium* cells; fungal cells, such as yeast cells; insect cells such as Drosophila 52 and Spodoptera Sf9 cells; animal cells such as CHO, COS and Bowes melanoma cells; and plant cells. Hosts for a great variety of expression constructs are well known, and those of skill will be enabled by the present disclosure readily to select a host for expressing a polypeptides in accordance with this aspect of the present invention.

Various mammalian cell culture systems can be employed for expression, as well. Examples of mammalian expression systems include the COS-7 lines of monkey kidney fibroblast (Gluzman et al., *Cell* 23: 175, 1991). Other cell lines capable of expressing a compatible vector include for example, the C127, 3T3, CHO, HeLa, human kidney 293 and BHK cell lines. In mammalian host cells, a number of viral-based expression systems may be utilized. In cases where an adenovirus is used as an expression vector, the polynucleotide sequence coding for HIAP3 may be ligated into an adenovirus transcription/translation complex consisting of the late promoter and tripartite leader sequence. Insertion in a nonessential E1 or E3 region of the viral genome will result in a viable virus capable of expressing HIAP3 in infected host cells (Logan and Shenk, *Proc. Natl. Acad. Sci. USA* 81:3655–59, 1984). In addition, transcription enhancers, such as the rouse sarcoma virus (RVS) enhancer, may be used to increase expression in mammalian host cells.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen USA (Valencia, Calif.); pBS vectors, Phagescript® vectors, Bluescript® vectors, pNH8A, pNHI6a, pNHI8A, pNH46A, available from Stratagene (LaJolla, Calif.); and ptrc99a, pK223-3, pKK233-3, pDR540, pRIT5 available from Pharmacia Biotech (Piscataway, N.J.). Most preferred is the pGEX-6P-3 vector, available from Pharmacia Biotech. Among preferred eukaryotic vectors are pWLNEO, pSV2CAT, pOG44, PXTI and pSG available from Stratagene; and PSVK3, pBPV, pMSG and pSVL available from Pharmacia Biotech. Most preferred are the vectors pcDNA3.1 Myc-His and pRc/CMV2 available from Introgene. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("cat") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-B and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the *E. coli* lacI and lacZ promoters, the T3 and T7 promoters, the T5 tac promoter, the lambda PR, PL promoters and the trp promoter. Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV") and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

Generally, recombinant expression vectors will include origins of replication, a promoter derived from a highly-expressed gene to direct transcription of a downstream structural sequence, and a selectable marker to permit isolation of vector containing cells after exposure to the vector.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell. Constructs in host cells can be used in a conventional manner to produce the gene product encoded by the recombinant sequence. Alternatively, the polypeptides of the present invention can be produced by direct peptide synthesis using solid-phase techniques (Stewart et al., *Solid-Phase Peptide Synthesis,* W. H. Freeman Co., San Francisco, 1969; Merrifield, J., *J. Am. Chem. Soc.* 85:2149–2154, 1963). In vitro protein synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. Various fragments of HIAP3 may be chemically synthesized separately and combined using chemical methods to produce the full length molecule.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., cited elsewhere herein.

Transcription of the DNA encoding the polypeptides of the present invention by higher eukaryotes may be increased by inserting an enhancer sequence into the vector. Enhancers are cisacting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulurn, into the periplasmic space or into the extracellular environment, appropriate secretion signals may be incorporated into the expressed polypeptide. The signals may be endogenous to the polypeptide or they may be heterologous signals. The polypeptide may be expressed in a modified form, such as a fusion protein, and may include not only secretion signals but also additional heterologous functional regions. Thus for instance, a region of additional amino acids, particularly charged amino acids, may be added to the N-terminus of the polypeptide to improve stability and persistence in the host cell, during purification or during subsequent handling and storage. Also, special regions also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. For example, when large quantities of HIAP3 are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the hiap3 coding sequence may be ligated into the vector in frame with sequence for the amino-terminal Met and the subsequent 7 residues of β-galactosidase so that a hybrid protein is produced; pIN vectors (Van Heede and Shuster, *J. Biol. Chem.* 264:5503–5509, 1989) and the like. PGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor Xa protease cleavage sites so that the cloned polypeptide of interest can be released from the GST moiety at will.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

The HIAP3 polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification. Various other methods of protein purification well known in the art include those described in Deutscher, M., *Methods in Enzymology,* Vol 182, Academic Press, San Diego, 1982; and Scopes, R., *Protein Purification: Principles and Practice* Springer-Verlag, New York, 1982.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Uses of HIAP3 polypeptides and the polynucleotides which encode them hiap3 polynucleotides and HIAP3 polypeptides may be used in accordance with the present invention for a variety of applications, particularly those that make use of the chemical and biological properties of HIAP3. Additional applications relate to diagnosis and to treatment of disorders of cells, tissues and organisms related to the presence of inappropriate apoptosis. These aspects of the invention are illustrated further by the following discussion and are described further within the body of the specification.

The rationale for the use of the polynucleotide and polypeptide sequences of the present invention is based in part on the chemical and structural homology between the HIAP3 disclosed herein and other IAP molecules. HIAP3 may be used in the diagnosis and treatment of conditions, disorders or diseases associated with abnormal or inappropriate apoptosis. These would include, but are not limited to, cancer and chronic viral infections, in which apoptosis is insufficient, and neurodegenerative disorders and chronic heart failure, which are characterized by premature apoptosis.

hiap3 polynucleotide sequences can be used for chromosome identification and as DNA probes.

HIAP3 polypeptides can be used to generate antibodies to HIAP3 which may be useful in detecting the levels of HIAP3 protein in cells and tissues.

Polynucleotides encoding HIAP3 may be useful in diagnostic assays for detecting the levels of polynucleotides encoding HIAP3 in cells and tissues.

In conditions associated with overexpression of HIAP3, such as cancer, it may be advantageous to suppress HIAP3 production, thus reducing HIAP3 levels. HIAP3 could be suppressed by administration of antisense oligonucleotides or ribozymes. Alternatively, antibodies specifically recognizing areas of the HIAP3 polypeptide which are responsible for its activity may be introduced to treat diseases or conditions associated with abnormal HIAP3 activity.

In conditions associated with underexpression of HIAP3, such as neurodegenerative disorders, it may be advantageous to increase HIAP3 levels. HIAP3 could be supplied to the patient using gene therapy, in which expression of HIAP3 polypeptide occurs in vivo within the patient following administration of suitable recombinant molecules containing polynucleotides encoding and expressing HIAP3 polypeptide.

Polynucleotide assays

This invention is also related to the use of the HIAP3 polynucleotides to detect complementary polynucleotides such as, for example, as a diagnostic reagent. Detection of a mutated form of HIAP3. associated with a dysfunction will provide a diagnostic tool that can add or define a diagnosis of a disease or susceptibility to a disease which results from under-expression, over-expression or altered expression of HIAP3, such as, for example, neoplasia and neurodegenerative disorders.

Individuals carrying mutations in the gene encoding HIAP3 may be detected at the DNA level by a variety of techniques. Polynucleotide samples for diagnosis may be obtained from a patient's cells, such as from blood, urine, saliva, tissue biopsy and autopsy material. The genomic DNA may be used directly for detection or may be amplified enzymatically by using PCR prior to analysis (Saiki et al., Nature, 324: 163–166, 1986). RNA or cDNA may also be used in the same ways. As an example, PCR primers complementary to the polynucleotide sequence encoding HIAP3 can be used to identify and analyze hiap3 expression and mutations. For example, deletions and insertions can be detected by a change in size of the amplified product in comparison to the normal genotype. Point mutations can be identified by hybridizing amplified DNA to radiolabeled hiap3 RNA or alternatively, radiolabeled hiap3 antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled polynucleotide or by automatic sequencing procedures with fluorescent tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see e.g., Myers et al., Science, 230: 1242, 1985).

Sequence changes at specific locations also may be revealed by nuclease protection assays, such as RNase and S1 protection or the chemical cleavage method (e.g., Catton et al., Proc. Natl. Acad. Sci., USA, 85:4397–4401, 1985).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA).

In addition to more conventional gel-electrophoresis and DNA sequencing, mutations also can be detected by in situ analysis.

Chromosome assays

The polynucleotide sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of an hiap3 gene. This can be accomplished using a variety of well known techniques and libraries which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with cDNA as short as 50 or 60 bases. For a review of this technique, see Verma et al., *Human Chromosomes: A Manual of Basic Techniques,* Pergamon Press, New York, 1988.

Once a sequence has been mapped to a precise chromosomal location, the physical position of the sequence on the chromosome can be correlated with genetic map data. Such data are found, for example, in V. McKusick, *Mendelian Inheritance in Man,* available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal: individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb). In situ hybridization of chromosomal preparations and physical mapping techniques such as linkage analysis using established chromosomal markers may be used for extending genetic maps. For example, an STS based map of the human genome was published by the Whitehead-MIT Center for Genomic Research (Hudson et al., *Science* 270:1945–1954, 1995). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT) has been crudely localized by genetic linkage to a particular genomic region, for example, AT to 11q22-23 (Gatti et al., *Nature* 336:577–580, 1988), any sequences mapping to that area may represent associated or regulatory genes for further investigation. The nucleotide sequence of the present invention may also be used to detect differences in the chromosomal location due to translocation, inversion, etc. among normal, carrier or affected individuals.

Polypeptide assays

The present invention also relates to a diagnostic assays such as quantitative and diagnostic assays for detecting levels of HIAP3 protein in cells and tissues, including determination of normal and abnormal levels. Thus, for instance, a diagnostic assay in accordance with the invention for detecting over-expression of HIAP3 protein compared to normal control tissue samples may be used to detect the presence of neoplasia, for example, tumors. Assay techniques that can be used to determine levels of a protein, such as an HIAP3 protein of the present invention, in a sample derived from a host are well-known to those of skill in the art. Such assay methods include radioimmunoassays (RIA), competitive-binding assays, western Blot analysis and enzyme-linked immunoabsorbant assays (ELISA), and fluorescent activated cell sorting (FACS). Among these ELISAs frequently are preferred. An ELISA assay initially comprises preparing an antibody specific to HIAP3, preferably a monoclonal antibody. In addition a reporter antibody generally is prepared which binds to the monoclonal antibody. The reporter antibody is attached to a detectable reagent such as a radioactive, fluorescent or enzymatic reagent, in this example horseradish peroxidase enzyme.

To carry out an ELISA a sample is removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any HIAP3 proteins attached to the polystyrene dish. Unbound monoclonal antibody is washed out with buffer. The reporter antibody linked to horseradish peroxidase is placed in the dish resulting in binding of the reporter antibody to any monoclonal antibody bound to HIAP3. Unattached reporter antibody is then washed out. Reagents for peroxidase activity, including a calorimetric substrate are then added to the dish. Immobilized peroxidase, linked to HIAP3 through the primary and secondary antibodies, produces a colored reaction product. The amount of color developed in a given time period indicates the amount of HIAP3 protein present in the sample. Quantitative results typically are obtained by reference to a standard curve.

A competition assay may be employed wherein antibodies specific to HIAP3 are attached to a solid support and labeled HIAP3 and a sample derived from the host are passed over the solid support and the amount of label detected attached to the solid support can be correlated to a quantity of HIAP3 in the sample.

These and other assays are described, among other places, in Hampton et al. (*Serological Methods, a Laboratory Manual,* APS Press, St Paul, Minn., 1990) and Maddox et al. (*J. Exp. Med.* 158:12111, 1983).

Antibodies

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, *Nature* 256: 495–497, 1975), the human B-cell hybridoma technique (Kozbor et al., *Immunology Today* 4: 72, 1983) and the EBV-hybridoma technique to produce human monoclonal antibodies (Cole et al., in *Monoclonal Antibodies and Cancer,* Alan R. Liss, Inc., 77–96, 1985).

In addition, techniques developed for the production of "chimeric antibodies", the splicing of mouse antibody genes to human antibody genes to obtain a molecule with appropriate antigen specificity and biological activity can be used (Morrison et al., *Proc. Natl. Acad. Sci. USA* 81:6851–6855, 1984; Neuberger et al., *Nature* 312:604–608, 1984; Takeda et al., *Nature* 314:452–454, 1985). Alternatively, techniques described for the production of single chain antibodies (U.S. Pat. No. 4,946,778) can be adapted to produce HIAP3-specific single chain antibodies.

Antibodies may also be produced by inducing in vivo production in the lymphocyte population or by screening recombinant immunoglobulin libraries or panels of highly specific binding reagents as disclosed in Orlandi et al. (*Proc. Natl. Acad. Sci. USA* 86:3833–3837, 1989) and Winter and Milstein (*Nature* 349:293–299, 1991).

Antibody fragments which contain specific binding sites for HIAP3 may also be generated. For example, such fragments include, but are not limited to the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse et al., *Science* 256:1270–1281, 1989).

The above-described antibodies may be employed to isolate or to identify clones expressing the polypeptide or purify the polypeptide of the present invention by attachment of the antibody to a solid support for isolation and/or purification by affinity chromatography.

Pharmaceutical Compositions and Administration

The present invention also relates to pharmaceutical compositions which may comprise hiap3 polynucleotides, HIAP3 proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

The present invention also relates to the administration of pharmaceutical compositions. Such administration is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxilliaries which facilitate processing of the active compounds into preparations which can be used pharmaceutically. Further details on techniques for formulation and administration may be found in the latest edition of *Remington's Pharmaceutical Sciences* (Ed. Maack Publishing Co, Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxilliaries, if desired, to obtain tablets or dragee cores. Suitable excipients are carbohydrate or protein fillers such as sugars, including lactose, sucrose, mannitol, or sorbitol; starch from corn, wheat, rice, potatoe, or other plants; cellulose such as methyl, cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol and/or titanium dioxide, lacquer solutions, and suitable organic solvents or solvent mixtures. Dyestuffs or pigments may be added to the tablets or dragee coatings for product identification or to characterize the quantity of active compound, ie. dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer's solution, or physiologically buffered saline. Aqueous injection suspensions may contain substances which increase viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture use or sale of pharmaceuticals or biological products, reflecting approval by the agency of the manufacture, use or sale of the product for human administration.

Manufacture and Storage

The pharmaceutical compositions of the present invention may be manufactured in a manner that is known in the art, e.g., by means of conventional mixing, dissolving, granulating, dragee-making, levigating, emulsifying, encapsulating, entrapping or lyophilizing processes.

The pharmaceutical composition may be provided as a salt and can be formed with may acids, including by not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labeled for treatment of an indicated condition. For administration of HIAP3, such labeling would include amount, frequency and method of administration.

Therapeutically Effective Dose.

Pharmaceutical compositions suitable for use in the present invention include compositions wherein the active ingredients are contained in an effective amount to achieve the intended purpose, i.e. treatment of a particular disease state characterized by inappropriate apoptosis. The determination of an effective dose is well within the capability of those skilled in the art.

For any compound, the therapeutically effective dose can be estimated initially either in cell culture assays, e.g., neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions which exhibit large therapeutic indices are preferred. The data obtained from cell culture assays and animal studies is used in formulating a range of dosage for human use. The dosage of such compounds lies preferably within a range of circulating concentrations what include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for polynucleotides than for proteins or their inhibitors. Similarly, delivery of polynucleotides or polypeptides will be specific to particular cells, conditions, locations, etc.

Gene Therapy

The hiap3 polynucleotides and HIAP3 polypeptides of the present invention may be employed in accordance with the present invention by expression of such polypeptides in vivo, in treatment modalities often referred to as "gene therapy."

Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct then may be isolated and introduced into a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Such vectors will include one or more promoters for expressing the polypeptide. Suitable promoters which may be employed include, but are not limited to, the retroviral LTR; the SV4O promoter; and the human cytomegalovirus (CMV) promoter (Miller et al., Biotechniques 7: 980–990, 1989), or any other promoter (e.g., cellular promoters such as eukaryotic cellular promoters including, but not limited to, the histone, RNA polymerase III, and β actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The polynucleotide sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus CMV) promoter; the respiratory syncytial virus (RSV) promoter; inducible promoters, such as the MMT promoter, the metallothionein promoter; heat shock promoters; the albumin promoter; the ApoAl promoter; human globin promoters; viral thymidine kinase promoters such as the Herpes Simplex thymidine kinase promoter; retroviral LTRs (including the modified retroviral LTRs herein above described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE5OI, PA317, Y-2, Y-AM, PAI2, T19-14X, VT-19-17-H2, YCRE, YCRIP, GP+E-86, GP+envAml 2, and DAN cell lines as described in Miller, A., *Human Gene Therapy* 1: 5–14, 1990. The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the polynucleotide sequence (s) encoding the polypeptides. Such retroviral vector particles then may be employed to transduce eukaryotic cells, either in vitro or in vivo. The transduced eukaryotic cells will express the polynucleotide(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Therapeutic use of antisense vectors and ribozymes

Expression vectors derived from retroviruses, adenovirus, herpes or vaccinia viruses, or from various bacterial plasmids, may be also be used for construction and delivery of recombinant vectors which will express anti-sense hiap3. See, for example, the techniques described in Sambrook et al. (supra) and Ausubel et al. (supra).

The polynucleotides comprising full length cDNA sequence and/or its regulatory elements enable researchers to use hiap3 polynucleotides as an investigative tool in sense (Youssoufian and Lodish, *Mol. Cell. Biol.* 13:98–104, 1993) or antisense (Eguchi, et al., *Annu. Rev. Biochem.* 60:631–652, 1991) regulation of gene function. Such technology is now well known in the art, and sense or antisense oligomers, or larger fragments, can be designed from various locations along the coding or control regions.

Genes encoding HIAP3 can be turned off by transfecting a cell or tissue with expression vectors which express high levels of a desired HIAP3 fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modification of gene expression can be obtained by designing antisense molecules, DNA or RNA, to control regions of hiap3, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix.pairing compromises the ability of the double helix to open sufficiently for the binding of polymerases, transcription factors, or regulatory molecules. Recent therapeutic advances using triplex DNA were reviewed by Gee, J. E. et al. (In Huber and Car, *Molecular and Immunologic Approaches,* Futura Publishing Co., Mt. Kisco, N.Y., 1994).

Ribozymes are enzymatic RNA molecules capable of catalyzing the specific cleavage of RNA (U.S. Pat. No. 4,987,071; WO 93/23057). The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of RNA encoding HIAP3.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays (Irie et al., *Advance. Pharmacol.* 40:207–257, 1997).

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription or DNA sequences encoding HIAP3. Such DNA sequences may be incorporated into a wide variety of vectors which suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecules or the use of phosphorothioate or 2' O-methyl rather than phosphodiesterase linkages within the backbone of the molecule. Increased stability can also be achieved by the inclusion of nontraditional bases such as inosine and queosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient as presented in U.S. Pat. Nos. 5,399,493 and 5,437,994, disclosed herein by reference. Delivery by transfection and by liposome are quite will known in the art.

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

All examples were carried out using standard techniques, which are well known and routine to those of skill in the art, except where otherwise described in detail. Routine molecular biology techniques of the following examples can be carried out as described in standard laboratory manuals, such as Sambrook et al., *Molecular Cloning: A Laboratory Manual*, 2nd Ed.; Cold Spring Harbor Laboratory Press, Cold Spring Harbor, N.Y., 1989.

Isolation of Human iap3 cDNA Clone

A 226 bp EST sequence (Incyte Clone # 1419118) was identified based on analysis of the Incyte EST database using the polypeptide consensus sequence of the BIR domain of IAP. tblastn database (GCG package) searches using the peptide sequence predicted from the EST sequence revealed a significant degree of similarity between amino acid residues 19 and 75 of this gene product and the partial BIR domain of human inhibitor of apoptosis protein 1(HIAP1). There is a 42% to 47% identity between this 57amino acid gene product and partial BIR1, BIR2 and BIR3 sequences of HIAP1, suggesting that the gene product is a homolog of HIAP1.

A. 5' and 3' RACE (5' and 3' rapid amplification of cDNA end).

Oligonucleotide primers derived from the EST sequence was used to clone 5'-end and 3'-end cDNA. Marathon-ready human fetal kidney cDNA was purchased from Clontech Inc. (South San Francisco) and used as template. RACE reactions were carried out according to the manufacturer's instructions (Clontech Inc).

Oligonucleotide primers used in 5'RACE are:

5'CCTTCCTGGCTCCTGGGCACTTTCAGA3' (SEQ ID NO: 3)

5'GCCCCCATAGCAGAAGAAGCACCTC3' (SEQ ID NO: 4)

5'GACGCAACTCCTCAGAGCCCATGCC3' (SEQ ID NO: 5)

Oligonucleotide primers used in 3'RACE are

5'GGCATGGGCTCTGAGGAGTTG3' (SEQ ID NO: 6)

5'CAAGGTGAGGTGCTTCTTCTGCTA3' (SEQ ID NO: 7)

The PCR products were cloned into pCRII vector (Invitrogen). A total of 12 clones were sequenced. 7 clones have sequences which overlapped with the EST sequence.

B. DNA and protein sequence analysis

The DNA sequences of the above clones and EST clone were assembled using GCG assemble program. The resulting contiguous DNA sequence was used to search databases. Two clones were identified in Incyte database and one clone from public EST database. One clone (2953985) was ordered from Incyte and sequenced. Sequencing data showed that the cDNA sequence contains 1337 bp. This cDNA sequence is designated hiap3. There is 169 bp in the 5' untranslated region and 274 bp in the 3' untranslated region flanking the coding region (FIGS. 1 (SEQ ID NO: 1) and 3).

The coding region consists of 894 bp. An open reading frame of 298 amino acid residues was identified. The initiation codon ATG is located at polynucleotide position 170, which has an adequate Kozak sequence with an upstream stop codon at polynucleotide position 110 (FIGS. 1 and 3).

Analysis of the predicted protein sequence (FIG. 2 (SEQ ID NO:2)) reveals a single BIR domain from amino acid position 88 to 155 (FIG. 4). There is approximately 50% identity of the BIR domain between HIAP3 and the third BIR domain of either human or mouse IAP1 or IAP2. Analysis using the Genetic Computer Group PileUp algorithm indicates very high homology with other members of the IAP family (FIGS. 4 & 5). HIAP3 has the BIR signature residues including three cysteines and a histidine. A RING domain containing a peptide sequence from aa position 240 to 289 was also identified, which has the signature cysteine, leucine and histidine residues (FIG. 4). There is 84% identity of the RING domain between HIAP3 and human HIAP-1. A PileUp analysis shows very high homology within the members of the family (FIG. 5)

2. Northern Blot Analysis

A 414 bp Ava1 fragment, isolated from a 5'RACE clone (#1-1L2 generated using primer 5'GCCCCCATAGCA-GAAGAAGCACCTC3' (SEQ ID NO: 4)) was used to probe Northern blots. This fragment was labeled with $^{32}$P-dCTP using high prime labeling kit purchased from Boehringer Mannheim. Human Multiple Tissue Northern Blot I and II, Human Fetal Tissue Blot, Human Immune System Tissue Blot (Clontech) and Human Multiple Tumor Tissue Blot (Biochain) were probed at high stringency following the supplier's instructions (Clontech). The results indicates that hiap3 is expressed mainly in placenta, lymph node, fetal kidney and kidney tumor. These experiments were confirmed using a second probe, a 387 bp NarI-KpnI fragment isolated from a second 5'RACE clone (#9-9-1, generated using primer 5'CCTTCCTGGCTCCTGGGCACTTTCAGA3'(SEQ ID NO: 3)).

Analysis of the Incyte database using the BLAST algorithm from the GCG package with the full length cDNA sequence of hiap3 generated a total of 9 EST clones (including the original EST clone) in the Incyte database. These clones are 2953985, 1419118, 1418580, 3842242, 4589046, 1529102, 3673370, 1520835 and EST92646. Three clones are from fetal kidney library, one clone from mast cell library, one clone from dendritic cell library, one clone from mononuclear cell derived from umbilical vein, one clone from placenta, one clone from bladder tumor, and one clone from skin tumor tissue. The distribution of these EST clones is similar to that found in the Northern blot analysis and suggests that HIAP3 may play a role in development, hematopoietic/immune system and tumor formation.

All publications and patents mentioned in the above specification are herein incorporated by reference. While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An isolated polynucleotide comprising a polynucleotide sequence having at least a 95% identity over its entire length to a nucleic acid selected from the group consisting of:

(a) a polynucleotide encoding a polypeptide of the amino acid sequence set forth in FIG. 2 (SEQ ID NO: 2);

(b) a polynucleotide encoding a polypeptide of amino acid 88 to amino acid 289 as set forth in FIG. 2 (SEQ ID NO: 2);

(c) a polynucleotide encoding a polypeptide of amino acid 88 to amino acid 155 as set forth in FIG. 2 (SEQ ID NO: 2); and (d) a polynucleotide which is fully complementary to the polynucleotide of (a), (b), or (c); and wherein said polypeptides (a)–(d) contain a BIR domain and wherein said polypeptides are apoptosis inhibitors.

2. The polynucleotide of claim 1 wherein the polynucleotide is DNA.

3. The polynucleotide of claim 1 wherein the polynucleotide is RNA.

4. The polynucleotide of claim 2 wherein the polynucleotide encodes the polypeptide comprising amino acids 1 to 298 as set forth in FIG. 2 (SEQ ID NO: 2).

5. The polynucleotide of claim 2 wherein the polynucleotide encodes the polypeptide comprising amino acid 88 to amino acid 289 as set forth in FIG. 2 (SEQ ID NO: 2).

6. The polynucleotide of claim 2 wherein the polynucleotide encodes the polypeptide comprising amino acid 88 to amino acid 155 as set forth in FIG. 2 (SEQ ID NO: 2).

7. The polynucleotide of claim 1 wherein the polynucleotide comprises the sequence as set forth in FIG. 1 (SEQ ID NO: 1) from nucleotide 1 to nucleotide 1337.

8. The polynucleotide of claim 1 wherein the polynucleotide comprises the sequence as set forth in FIG. 1 (SEQ ID NO: 1) from nucleotide 170 to nucleotide 1064.

9. A vector comprising the polynucleotide of claim 2.

10. A host cell comprising the vector of claim 9.

11. A method of producing a polypeptide comprising expressing from the host cell of claim 10 the polypeptide encoded by the polynucleotide.

12. The method of claim 11 wherein the polypeptide comprises amino acid 1 to amino acid 298 as set forth in FIG. 2 (SEQ ID NO: 2).

13. The method of claim 11 wherein the polypeptide comprises amino acid 88 to amino acid 289 as set forth in FIG. 2 (SEQ ID NO: 2).

14. The method of claim 11 wherein the polypeptide comprises amino acid 88 to amino acid 155 as set forth in FIG. 2 (SEQ ID NO: 2).

15. A method of producing a polypeptide wherein the polypeptide comprises the amino acid sequence shown in FIG. 2 (SEQ ID NO: 2), the method comprising the steps of:

(a) culturing the host cell of claim 10 under conditions whereby the polypeptide is expressed; and (b) recovering the polypeptide from the culture.

16. A method for producing a cell which expresses a polypeptide comprising genetically engineering the cell with the vector of claim 9.

17. An isolated polynucleotide wherein the polynucleotide encodes a polypeptide comprising amino acids 1 to 298 as set forth in FIG. 2 (SEQ ID NO: 2), wherein said polypeptide is an apoptosis inhibitor.

* * * * *

SEQUENCE LISTING

```
<160> NUMBER OF SEQ ID NOS: 7

<210> SEQ ID NO 1
<211> LENGTH: 1337
<212> TYPE: DNA
<213> ORGANISM: Homo sapiens
<220> FEATURE:
<221> NAME/KEY: CDS
<222> LOCATION: (170)..(1066)

<400> SEQUENCE: 1
gggatactcc cctcccaggg tgtctggtgg caggcctgtg cctatccctg ctgtcccag         60 ggtgggcccc gggggtcagg agctccagaa gggccagctg ggcatattct gagattggcc       120
atcagccccc atttctgctg caaacctggt cagagccagt gttccctcc atg gga cct       178
                                                      Met Gly Pro
                                                        1 aaa gac agt gcc aag tgc ctg cac cgt gga cca cag ccg agc cac tgg        226
Lys Asp Ser Ala Lys Cys Leu His Arg Gly Pro Gln Pro Ser His Trp
        5                  10                  15 gca gcc ggt gat ggt ccc acg cag gag cgc tgt gga ccc cgc tct ctg        274
Ala Ala Gly Asp Gly Pro Thr Gln Glu Arg Cys Gly Pro Arg Ser Leu
 20                  25                  30                  35 ggc agc cct gtc cta ggc ctg gac acc tgc aga gcc tgg gac cac gtg        322
Gly Ser Pro Val Leu Gly Leu Asp Thr Cys Arg Ala Trp Asp His Val
                 40                  45                  50 gat ggg cag atc ctg ggc cag ctg cgg ccc ctg aca gag gag gaa gag        370
Asp Gly Gln Ile Leu Gly Gln Leu Arg Pro Leu Thr Glu Glu Glu Glu
             55                  60                  65 gag gag ggc gcc ggg gcc acc ttg tcc agg ggg cct gcc ttc ccc ggc        418
Glu Glu Gly Ala Gly Ala Thr Leu Ser Arg Gly Pro Ala Phe Pro Gly
         70                  75                  80 atg ggc tct gag gag ttg cgt ctg gcc tcc ttc tat gac tgg ccg ctg        466
Met Gly Ser Glu Glu Leu Arg Leu Ala Ser Phe Tyr Asp Trp Pro Leu
     85                  90                  95 act gct gag gtg cca ccc gag ctg ctg gct gct gcc ggc ttc ttc cac        514
Thr Ala Glu Val Pro Pro Glu Leu Leu Ala Ala Ala Gly Phe Phe His
100                 105                 110                 115 aca ggc cat cag gac aag gtg agg tgc ttc ttc tgc tat ggg ggc ctg        562
Thr Gly His Gln Asp Lys Val Arg Cys Phe Phe Cys Tyr Gly Gly Leu
                120                 125                 130 cag agc tgg aag cgc ggg gac gac ccc tgg acg gag cat gcc aag tgg        610
Gln Ser Trp Lys Arg Gly Asp Asp Pro Trp Thr Glu His Ala Lys Trp
            135                 140                 145 ttc ccc agc tgt cag ttc ctg ctc cgg tca aaa gga aga gac ttt gtc        658
Phe Pro Ser Cys Gln Phe Leu Leu Arg Ser Lys Gly Arg Asp Phe Val
        150                 155                 160
```

```
cac agt gtg cag gag act cac tcc cag ctg ctg ggc tct tgg gac ccg      706
His Ser Val Gln Glu Thr His Ser Gln Leu Leu Gly Ser Trp Asp Pro
    165                 170                 175 tgg gaa gaa ccg gaa gac gca gcc cct gtg gcc ccc tcc gtc cct gcc      754
Trp Glu Glu Pro Glu Asp Ala Ala Pro Val Ala Pro Ser Val Pro Ala
180                 185                 190                 195 tct ggg tac cct gag ctg ccc aca ccc agg aga gag gtc cag tct gaa      802
Ser Gly Tyr Pro Glu Leu Pro Thr Pro Arg Arg Glu Val Gln Ser Glu
                200                 205                 210 agt gcc cag gag cca gga ggg gtc agt cca gcc gag gcc cag agg gcg      850
Ser Ala Gln Glu Pro Gly Gly Val Ser Pro Ala Glu Ala Gln Arg Ala
            215                 220                 225 tgg tgg gtt ctt gag ccc cca gga gcc agg gat gtg gag gcg cag ctg      898
Trp Trp Val Leu Glu Pro Pro Gly Ala Arg Asp Val Glu Ala Gln Leu
        230                 235                 240 cgg cgg ctg cag gag gag agg acg tgc aag gtg tgc ctg gac cgc gcc      946
Arg Arg Leu Gln Glu Glu Arg Thr Cys Lys Val Cys Leu Asp Arg Ala
    245                 250                 255 gtg tcc atc gtc ttt gtg ccg tgc ggc cac ctg gtc tgt gct gag tgt      994
Val Ser Ile Val Phe Val Pro Cys Gly His Leu Val Cys Ala Glu Cys
260                 265                 270                 275 gcc ccc ggc ctg cag ctg tgc ccc atc tgc aga gcc ccc gtc cgc agc     1042
Ala Pro Gly Leu Gln Leu Cys Pro Ile Cys Arg Ala Pro Val Arg Ser
                280                 285                 290 cgc gtg cgc acc ttc ctg tcc tag gccaggtgcc atggccggcc aggtgggctg    1096
Arg Val Arg Thr Phe Leu Ser
            295 cagagtgggc tccctgcccc tctctgcctg ttctggactg tgttctgggc ctgctgagga   1156 tggcagagct ggtgtccatc cagcactgac cagccctgat tccccgacca ccgcccaggg   1216 tggagaagga ggcccttgct tggcgtgggg gatggcttaa ctgtacctgt ttggatgctt   1276 ctgaatagaa ataaagtggg ttttccctgg aggtacccag caaaaaaaaa aaaaaaaaaa   1336 a                                                                  1337

<210> SEQ ID NO 2
<211> LENGTH: 298
<212> TYPE: PRT
<213> ORGANISM: Homo sapiens

<400> SEQUENCE: 2

Met Gly Pro Lys Asp Ser Ala Lys Cys Leu His Arg Gly Pro Gln Pro
 1               5                  10                  15

Ser His Trp Ala Ala Gly Asp Gly Pro Thr Gln Glu Arg Cys Gly Pro
             20                  25                  30

Arg Ser Leu Gly Ser Pro Val Leu Gly Leu Asp Thr Cys Arg Ala Trp
         35                  40                  45

Asp His Val Asp Gly Gln Ile Leu Gly Gln Leu Arg Pro Leu Thr Glu
     50                  55                  60

Glu Glu Glu Glu Gly Ala Gly Ala Thr Leu Ser Arg Gly Pro Ala
 65                  70                  75                  80

Phe Pro Gly Met Gly Ser Glu Glu Leu Arg Leu Ala Ser Phe Tyr Asp
                 85                  90                  95

Trp Pro Leu Thr Ala Glu Val Pro Pro Glu Leu Leu Ala Ala Ala Gly
            100                 105                 110

Phe Phe His Thr Gly His Gln Asp Lys Val Arg Cys Phe Phe Cys Tyr
        115                 120                 125

Gly Gly Leu Gln Ser Trp Lys Arg Gly Asp Asp Pro Trp Thr Glu His
```

```
                    130                 135                 140
Ala Lys Trp Phe Pro Ser Cys Gln Phe Leu Leu Arg Ser Lys Gly Arg
145                 150                 155                 160

Asp Phe Val His Ser Val Gln Glu Thr His Ser Gln Leu Leu Gly Ser
                165                 170                 175

Trp Asp Pro Trp Glu Glu Pro Glu Asp Ala Ala Pro Val Ala Pro Ser
            180                 185                 190

Val Pro Ala Ser Gly Tyr Pro Glu Leu Pro Thr Pro Arg Arg Glu Val
        195                 200                 205

Gln Ser Glu Ser Ala Gln Glu Pro Gly Gly Val Ser Pro Ala Glu Ala
    210                 215                 220

Gln Arg Ala Trp Trp Val Leu Glu Pro Pro Gly Ala Arg Asp Val Glu
225                 230                 235                 240

Ala Gln Leu Arg Arg Leu Gln Glu Glu Arg Thr Cys Lys Val Cys Leu
                245                 250                 255

Asp Arg Ala Val Ser Ile Val Phe Val Pro Cys Gly His Leu Val Cys
                260                 265                 270

Ala Glu Cys Ala Pro Gly Leu Gln Leu Cys Pro Ile Cys Arg Ala Pro
            275                 280                 285

Val Arg Ser Arg Val Arg Thr Phe Leu Ser
    290                 295
```

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 3
ccttcctggc tcctgggcac tttcaga     27

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 4
gcccccatag cagaagaagc acctc     25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 5
gacgcaactc ctcagagccc atgcc     25

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 6
ggcatgggct ctgaggagtt g     21

-continued

```
<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 7
caaggtgagg tgcttcttct gcta                                          24
```